(12) United States Patent
Stearns et al.

(10) Patent No.: US 9,289,233 B2
(45) Date of Patent: Mar. 22, 2016

(54) LOW-PROFILE SURGICAL ACCESS DEVICES WITH ANCHORING

(75) Inventors: Ralph Stearns, Bozrah, CT (US); Kurt Azarbarzin, Fairfield, CT (US); James R. Parys, Cheshire, CT (US)

(73) Assignee: SurgiQuest, Inc., Milford, CT (US)

( * ) Notice: Subject to any disclaimer, the term of this patent is extended or adjusted under 35 U.S.C. 154(b) by 1492 days.

(21) Appl. No.: 12/577,189

(22) Filed: Oct. 11, 2009

(65) Prior Publication Data

US 2010/0185057 A1    Jul. 22, 2010

Related U.S. Application Data

(63) Continuation of application No. PCT/US2009/060299, filed on Oct. 10, 2009.

(60) Provisional application No. 61/104,475, filed on Oct. 10, 2008.

(51) Int. Cl.
*A61B 1/32* (2006.01)
*A61B 17/34* (2006.01)
(Continued)

(52) U.S. Cl.
CPC .............. *A61B 17/3417* (2013.01); *A61B 17/02* (2013.01); *A61M 39/0247* (2013.01); *A61B 17/3423* (2013.01); *A61B 17/3431* (2013.01);
(Continued)

(58) Field of Classification Search
CPC ........... A61B 17/3423; A61B 17/3474; A61B 17/02; A61B 17/3417; A61B 17/3431; A61B 17/3498; A61B 17/3421
USPC .................................. 600/201–202, 204–208
See application file for complete search history.

(56) References Cited

U.S. PATENT DOCUMENTS 5,002,557 A * 3/1991 Hasson ..................... 606/191
5,290,249 A   3/1994 Foster et al.
(Continued)

FOREIGN PATENT DOCUMENTS

JP    2005506144 A    3/2005
JP    2005110978 A    4/2005
(Continued)

OTHER PUBLICATIONS

International Search Report dated May 29, 2010 for the corresponding PCT Application.
(Continued)

*Primary Examiner* — Jacqueline Johanas
(74) *Attorney, Agent, or Firm* — Locke Lord LLP; Scott D. Wofsy

(57) ABSTRACT

A surgical access device includes a proximal housing having proximal and distal end portions, the distal end portion of the housing being configured and adapted to engage a proximal portion of a flexible wound retractor. The proximal housing can be provided with a plenum chamber being defined therein, the plenum chamber being in fluid communication with at least one nozzle. The nozzle is preferably configured to direct pressurized fluid in an axial direction from the plenum chamber into a central bore of the surgical access device to provide a constant gaseous seal around a surgical instrument inserted therethrough, while inhibiting a loss of pressurized fluid from the body cavity therethrough. The plenum chamber can be adapted and configured to receive pressurized fluid and conduct the pressurized fluid to the at least one nozzle.

1 Claim, 22 Drawing Sheets

(51) Int. Cl.
*A61B 17/02* (2006.01)
*A61M 39/02* (2006.01)
*A61M 39/04* (2006.01)

(52) U.S. Cl.
CPC ......... *A61B 17/3474* (2013.01); *A61B 17/3498* (2013.01); *A61B 2017/3445* (2013.01); *A61B 2017/3484* (2013.01); *A61M 39/045* (2013.01); *A61M 2039/0261* (2013.01); *A61M 2039/0264* (2013.01); *A61M 2039/0276* (2013.01); *A61M 2039/0279* (2013.01)

(56) References Cited

U.S. PATENT DOCUMENTS

| | | | |
|---|---|---|---|
| 5,366,446 | A | 11/1994 | Tal et al. |
| 5,545,179 | A * | 8/1996 | Williamson, IV ............ 606/213 |
| 5,720,759 | A | 2/1998 | Green et al. |
| 2003/0014076 | A1 * | 1/2003 | Mollenauer et al. .......... 606/213 |
| 2006/0247498 | A1 * | 11/2006 | Bonadio et al. ............... 600/208 |
| 2006/0247500 | A1 * | 11/2006 | Voegele et al. ............... 600/208 |
| 2006/0258899 | A1 | 11/2006 | Gill et al. |
| 2007/0088274 | A1 * | 4/2007 | Stubbs et al. ............ 604/164.01 |
| 2007/0088275 | A1 | 4/2007 | Stearns et al. |
| 2009/0137943 | A1 | 5/2009 | Stearns et al. |

FOREIGN PATENT DOCUMENTS

| | | |
|---|---|---|
| JP | 2007-044395 A | 2/2007 |
| WO | WO-9929250 A1 | 6/1999 |
| WO | WO-2006040748 A1 | 4/2006 |
| WO | WO-2008093313 A1 | 8/2008 |
| WO | WO-2010042915 A2 | 4/2010 |
| WO | PCT-2010-051955 | 5/2011 |

OTHER PUBLICATIONS

Office Action for Korean Patent Application No. 1020117009618, dated Oct. 8, 2015.

Office Action issued Sep. 17, 2013 for corresponding JP Application No. 2011-531240 including English translation.

* cited by examiner

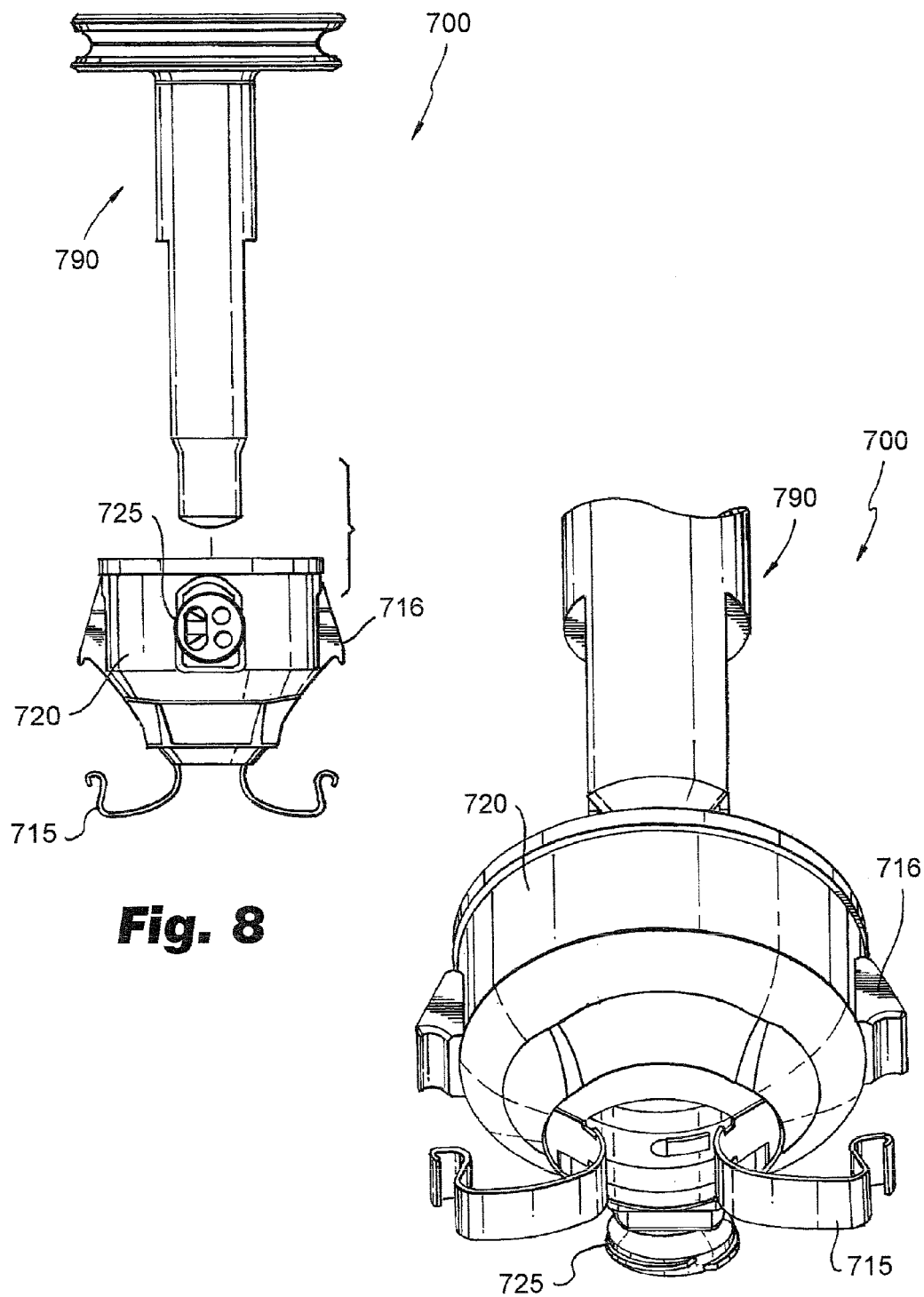

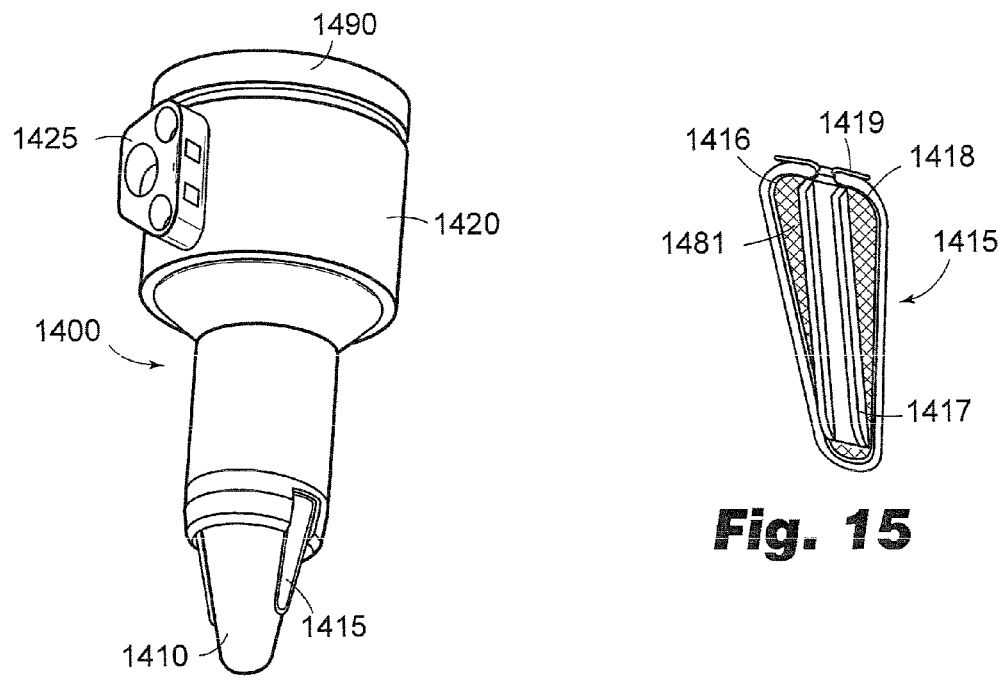
Fig. 14
Fig. 15
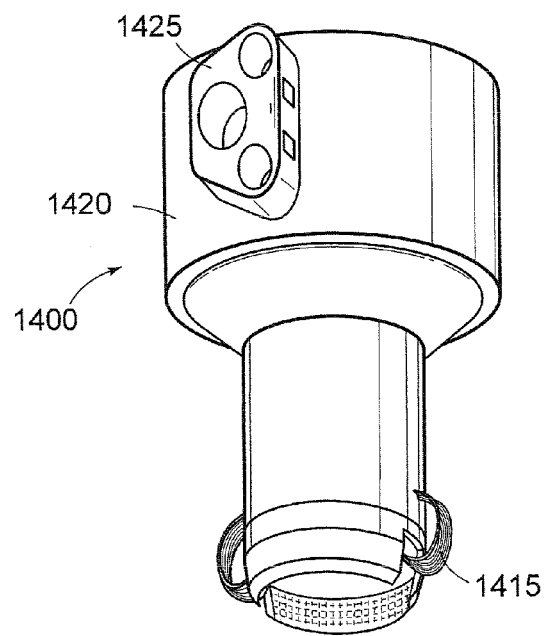
Fig. 16

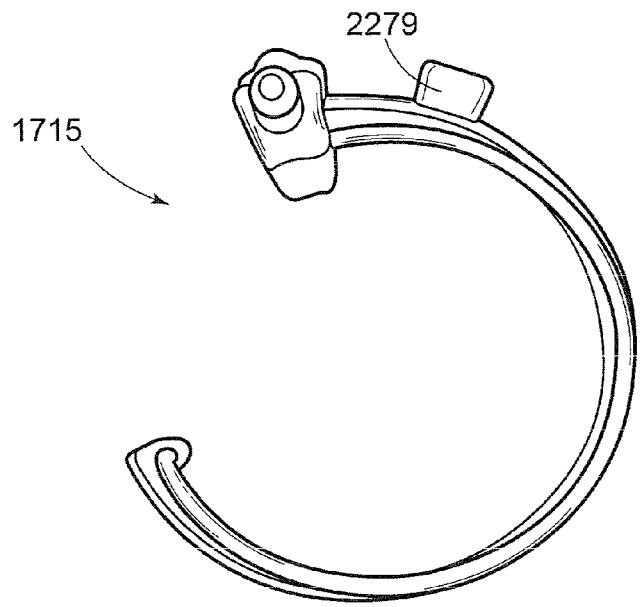
Fig. 24
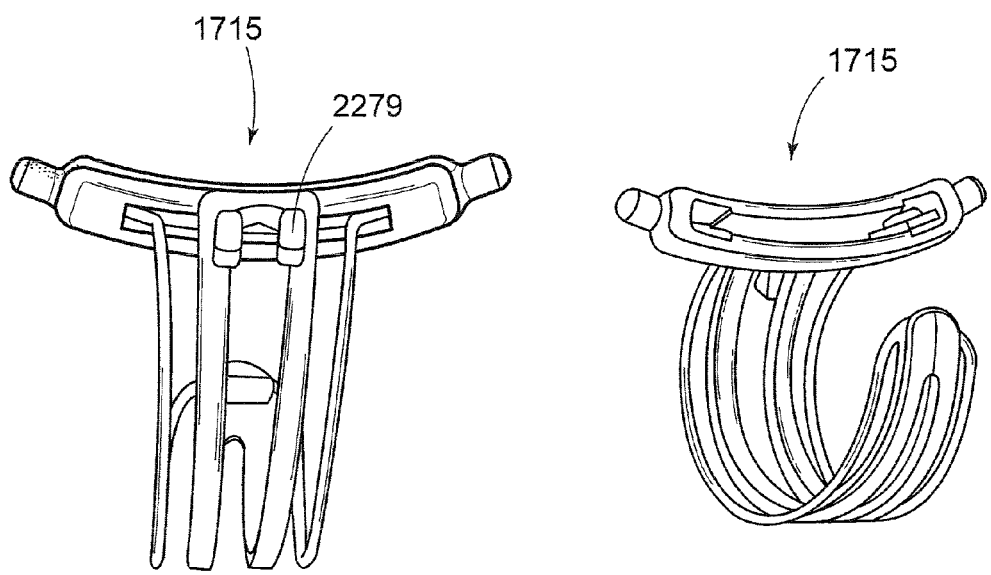
Fig. 25  Fig. 26

LOW-PROFILE SURGICAL ACCESS DEVICES WITH ANCHORING

CROSS-REFERENCE TO RELATED APPLICATIONS

This application is a continuation application of PCT/US09/60299, filed Oct. 10, 2009, which application claims the benefit of priority to U.S. Patent Application Ser. No. 61/104,475, filed 10 Oct. 2008. This application is also related to U.S. Pat. Nos. 7,182,752, 7,338,473, and 7,285,112, U.S. Patent Application Publication Number US 2007/0088275 and PCT application number PCT/US07/88017, published as Pub. No. WO 2008/077080. Each of the foregoing patents and applications is incorporated herein by reference in its entirety.

FIELD OF THE INVENTION

The present invention relates to surgical access devices for performing minimally-invasive surgical procedures. Particularly, the present invention is directed to surgical access devices that are particularly adapted to securely anchoring in an incision, such as one made through the abdominal wall of a patient. The present invention is also directed to such surgical access devices that include a non-mechanical pressure barrier for inhibiting loss of peritoneal pressure under abdominal insufflation.

DESCRIPTION OF RELATED ART

A variety of access devices are known in the art for accessing a surgical site, such as the abdominal cavity. Typically, ensuring that such access devices stay securely mounted in the abdominal wall without causing excessive trauma is a primary goal. The present invention provides various solutions to these problems.

SUMMARY OF THE INVENTION

The purpose and advantages of the present invention will be set forth in and apparent from the description that follows.

To achieve these and other advantages and in accordance with the purpose of the invention, as embodied, the invention includes, in one aspect, a surgical access device having proximal and distal end portions and an access tube extending distally from the distal end of the housing. The access tube is adapted and configured to extend at least partially though an incision formed in the abdominal wall of a patient and has a hyperbolic shape in cross section and an expanded-diameter distal portion to inhibit removal from an incision. A plenum chamber can be defined within the housing in fluid communication with at least one nozzle, and be configured to direct pressurized fluid in an axial direction from the plenum chamber into a central bore of the access tube to provide a constant gaseous seal around a surgical instrument inserted therethrough, while inhibiting a loss of pressurized fluid from the body cavity therethrough. The plenum chamber can be adapted and configured to receive pressurized fluid and conduct the pressurized fluid to the at least one nozzle. The plenum chamber can have an inlet port for communicating with a source of pressurized fluid. A pressure sensing chamber can be defined within the housing, and be adapted and configured to be in fluid communication with the abdominal cavity of the patient to facilitate sensing of abdominal pressure. The pressure sensing chamber can include an outlet port for communicating with a pressure sensor of a connected system. The sensing chamber can be in fluid communication with a sensing channel defined in the access tube of the surgical access device.

The nozzle can be defined by a gap formed between an outer periphery of a nozzle insert disposed within the proximal housing and an inner periphery of a substantially annular insert disposed within the proximal housing.

In accordance with another aspect of the invention, a surgical access device is provided which includes a proximal housing having proximal and distal end portions, the distal end portion of the housing being configured and adapted to engage a proximal portion of a flexible wound retractor. The proximal housing can be provided with a plenum chamber being defined therein, the plenum chamber being in fluid communication with at least one nozzle. The nozzle is preferably configured to direct pressurized fluid in an axial direction from the plenum chamber into a central bore of the surgical access device to provide a constant gaseous seal around a surgical instrument inserted therethrough, while inhibiting a loss of pressurized fluid from the body cavity therethrough. The plenum chamber can be adapted and configured to receive pressurized fluid and conduct the pressurized fluid to the at least one nozzle.

It is to be understood that both the foregoing general description and the following detailed description are exemplary and are intended to provide a non-limiting explanation of the invention.

BRIEF DESCRIPTION OF THE DRAWINGS

The accompanying drawings, which are incorporated in and constitute part of this specification, are included to illustrate and provide a further understanding of the method and system of the invention. Together with the description, the drawings serve to explain the principles of the invention, wherein:

FIGS. 2-6 illustrate a second exemplary embodiment of a surgical access device in accordance with the invention, which is adapted for use with flexible wound retractors and the like;

FIGS. 7-11 illustrate a third exemplary embodiment of a surgical access device in accordance with the invention, having opposed distal spring clips for engaging an abdominal wall of a patient;

FIGS. 14-16 illustrate a fifth exemplary embodiment of a surgical access device in accordance with the invention, having opposed deployable anchor elements;

FIGS. 17-26 illustrate a sixth exemplary embodiment of surgical access devices in accordance with the invention, having circumferentially arranged deployable anchor elements;

DETAILED DESCRIPTION

Reference will now be made in detail to the presently preferred embodiments of the invention, examples of which are illustrated in the accompanying drawings. The related methods of the invention will be described in conjunction with the detailed description of the devices.

Figure 1:
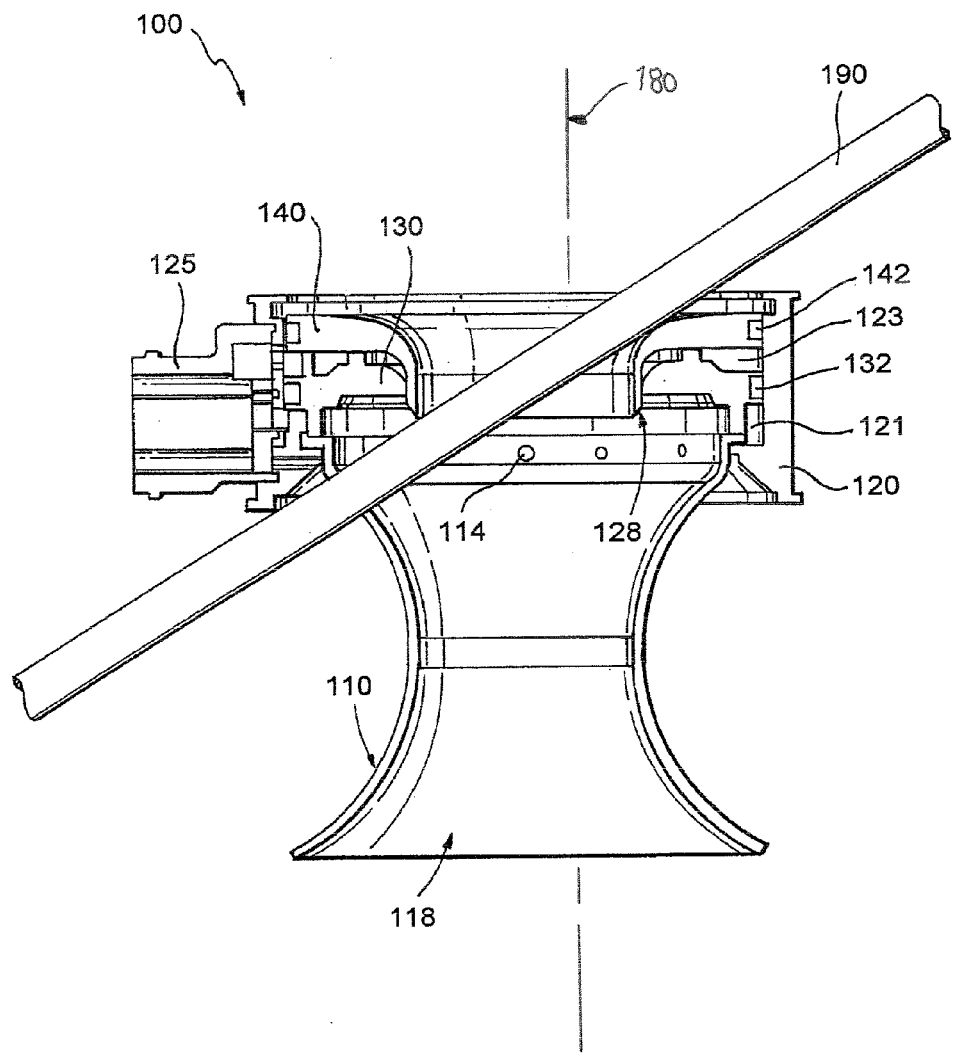
FIG. 1 is a cross sectional view of one embodiment of an example surgical access device in accordance with the invention, having a substantially hyperbolic flexible body tube.
Figure 2:
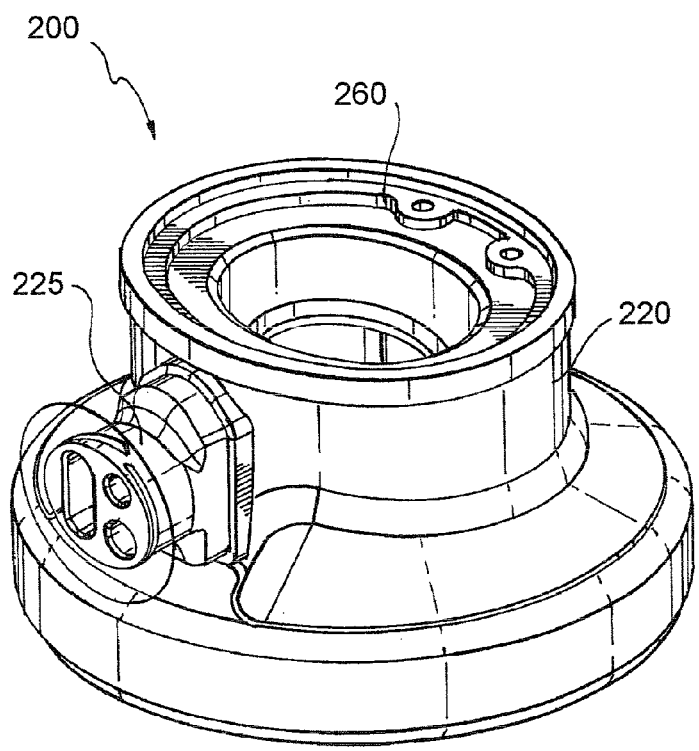
Figure 3:
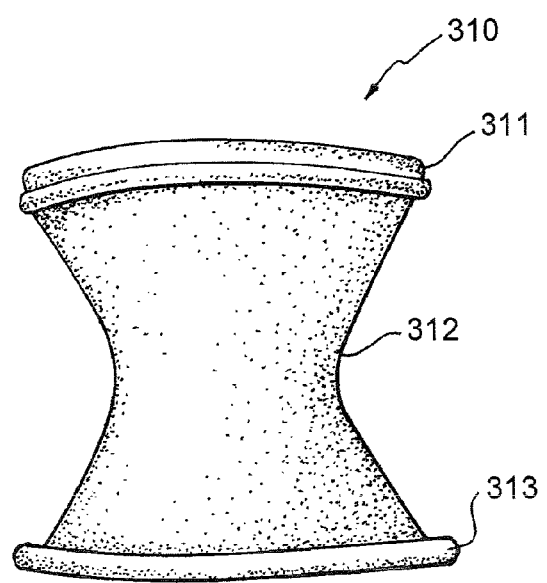

In accordance with the invention, and as illustrated in FIG. 1, a surgical access device 100 is provided, which is advantageously has a relatively low profile, allowing surgical instruments 190 inserted therethrough to be less restricted in movement than with more conventional surgical access devices. The access device 100 includes a housing 120, and a compliant access tube 110 extending distally from the distal end of the housing 120. The access tube 110 is adapted and configured to extend at least partially though an incision formed in the abdominal wall of a patient. In the illustrated embodiment, the access tube 110 has hyperbolic shape in cross section. An expanded-diameter distal portion of the access tube 110 inhibits removal of the access device 100 from the incision formed in the patient. In accordance with the invention, the length of the access tube 110 can be sufficiently long so as to extend fully though the abdominal wall of the patient and into the peritoneal space.

In accordance with the invention, the access device 100 can further include insufflation capability, can be adapted and configured to form a fluidic seal or barometric barrier around an instrument inserted therethrough and/or can be adapted to facilitate recirculation of insufflation gasses. Details of such capabilities are set forth in U.S. Pat. No. 7,182,752, U.S. Pat. No. 7,285,112, U.S. Pat. No. 7,338,473, U.S. Patent Publication No. US 2007/0088275 and PCT Publication No. WO 2008/077080, which documents are incorporated herein by reference in their entirety.

As illustrated in FIG. 1, for example, the surgical access device 100 can include an a pressurized fluid plenum 123 defined within the housing 120. In the illustrated embodiment, the plenum 123 is defined between the housing 120, a lower insert 130 and an upper insert 140. The plenum 123 is in fluid communication with at least one nozzle 128, and is configured to direct pressurized fluid in a substantially axial direction from the plenum 123 into a central lumen 118 of the access tube 110 to provide a constant gaseous seal around a surgical instrument inserted therethrough, and/or across the lumen 118 when an instrument is not inserted therethrough, for example.

Similarly, as illustrated, a recirculation chamber 121 can be defined in the access device 100, between the housing 120 and the lower insert 130. One or more sealing elements, such as resilient O-rings or the like, can be provided in seats 132, 142, which are formed respectively in each of the first and second inserts 130, 140. One or more openings 114 can be provided between the lumen 118 and the recirculation chamber 121 to allow gasses to pass into the recirculation chamber 121.

One or more additional chambers or other fluid conduits can further be provided, to facilitate fluid communication between a pressure-sensing device and/or a surgical insufflator, and the operative site. A fluid conduit can be formed within the wall of or on the inner or outer surfaces of the access tube 110. Alternatively, a separate tube can be passed though the lumen 118 for such purpose, if so desired. In still alternate embodiments, and as illustrated in the embodiment of FIGS. 2-6 for example, a pressure sensing and/or insufflation aperture 424 can simply be in fluid communication with the upper portion of the lumen 418.

As illustrated, a connection 125 is provided on the housing 120, and has at least one channel formed therein, in fluid communication with one of the aforementioned chambers and/or conduits. It is in fluid communication with such chambers and/or conduits by passages formed therein and in the housing 120. The connection 125 facilitates connection of multiple conduits, which may be embodied in a single set, to the access device 100 quickly and simply. The conduits, in-turn are connected to the appropriate equipment, including insufflation devices, recirculation devices and the like.

If desired, the housing 120 and the access tube 110 can be detachable from one another. The access tube 110 can be provided in assorted lengths and shapes, and with assorted features, as desired or required. Accordingly, a surgeon can decide before or during a procedure what length or diameter access tube 110 to use, and can attach it to the body 120 of the access device. Alternatively, a range of access devices of varying diameters, lengths and having varying features can be provided fully assembled to be available to the surgeon.

As set forth above, the illustrated cross-section of the access tube 110, which is taken in a plane parallel to the longitudinal axis 180 of the access device 100 is hyperbolic, and in three-dimensions is shaped as a hyperboloid of revolution. In cross-section, in a plane perpendicular to the central axis 180, for example, the cross-section can be circular, oval, elliptical or otherwise oblong in shape.

As illustrated in FIGS. 2-6, a surgical access device 200 in accordance with the invention can be adapted and configured for use with any desired tubular surgical access device, such as a flexible wound retractor 310 (FIG. 3), for example. Example wound retractors are set forth in U.S. Pat. Nos. 5,524,644, 3,347,226, 3,347,227, 5,159,921, 5,524,644, 6,450,983, 6,254,534, 6,846,287, 5,672,168, 5,906,577, 6,142,936, 5,514,133, 7,238,154, 6,945,932, 6,908,430, 6,972,026, 5,741,298, or 6,945,932, which disclosures are incorporated herein by reference in their entirety.

In such embodiments, the wound retractor can be inserted through an incision formed in the patient, and secured by any suitable means. The body 120 can then be secured, such as by interference fit, friction fit, clamps, straps or otherwise secured to the proximal end of the wound retractor, for the purpose of providing insufflation, recirculation and/or filtration and/or fluidic sealing capability to prevent loss of abdominal pressure when insufflated, without introducing a mechanical seal.

Figure 4:
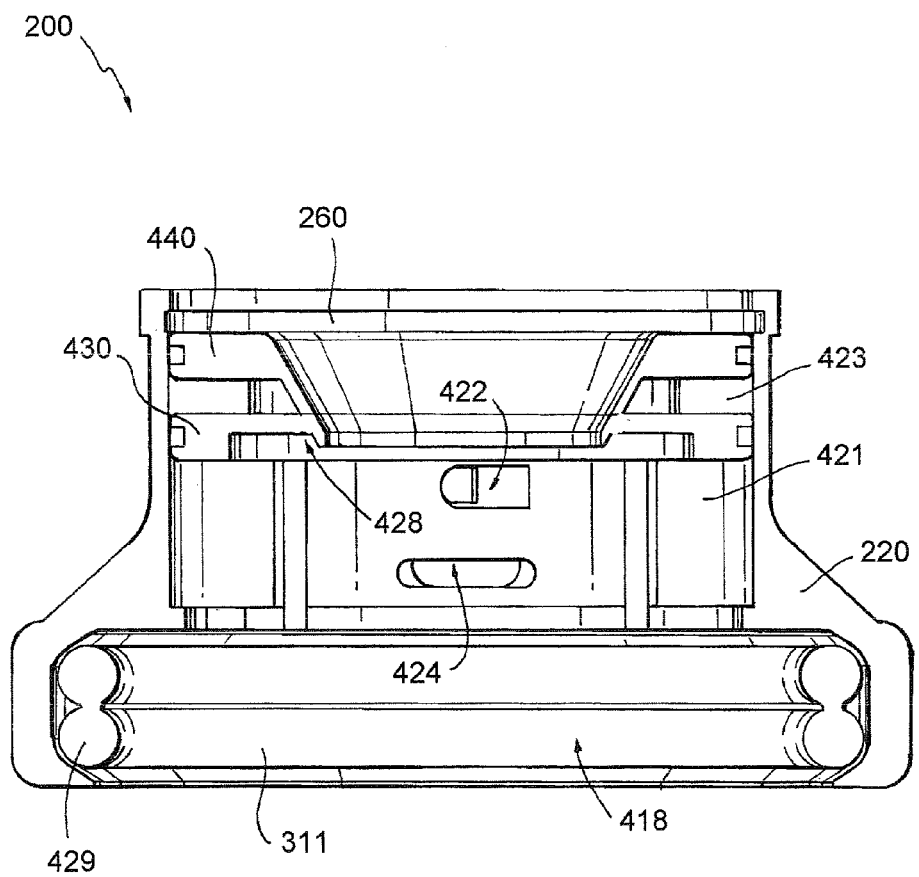
Figure 5A:
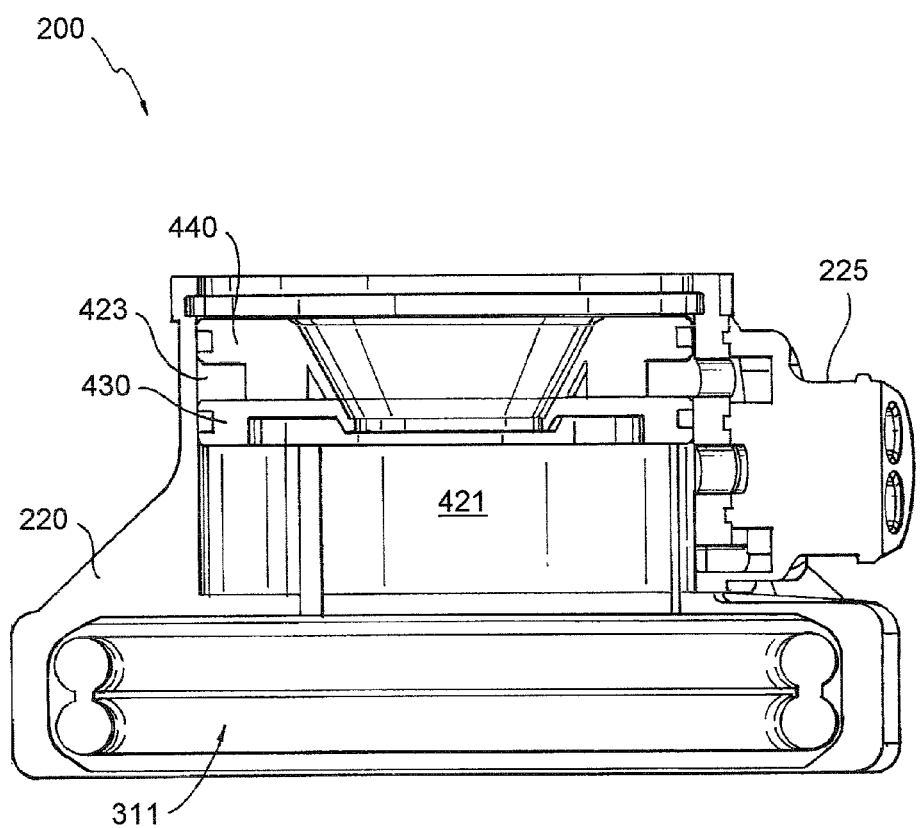
Figure 5B:
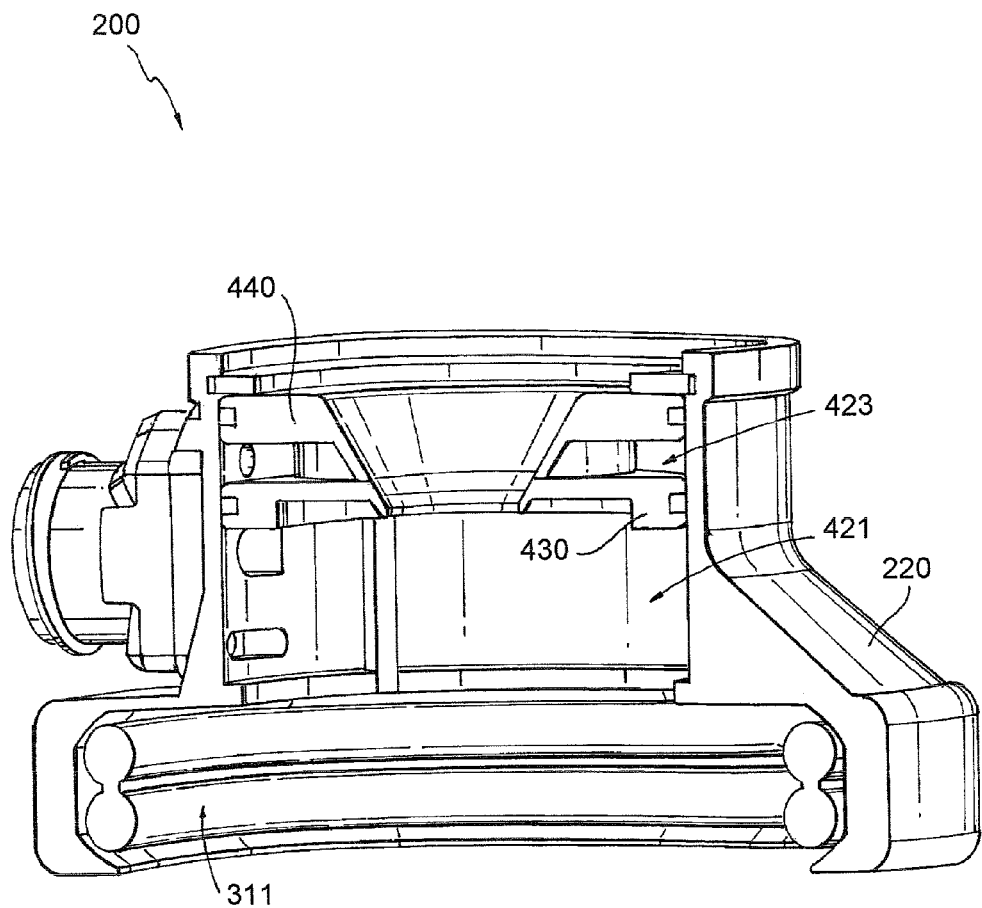
Figure 6:
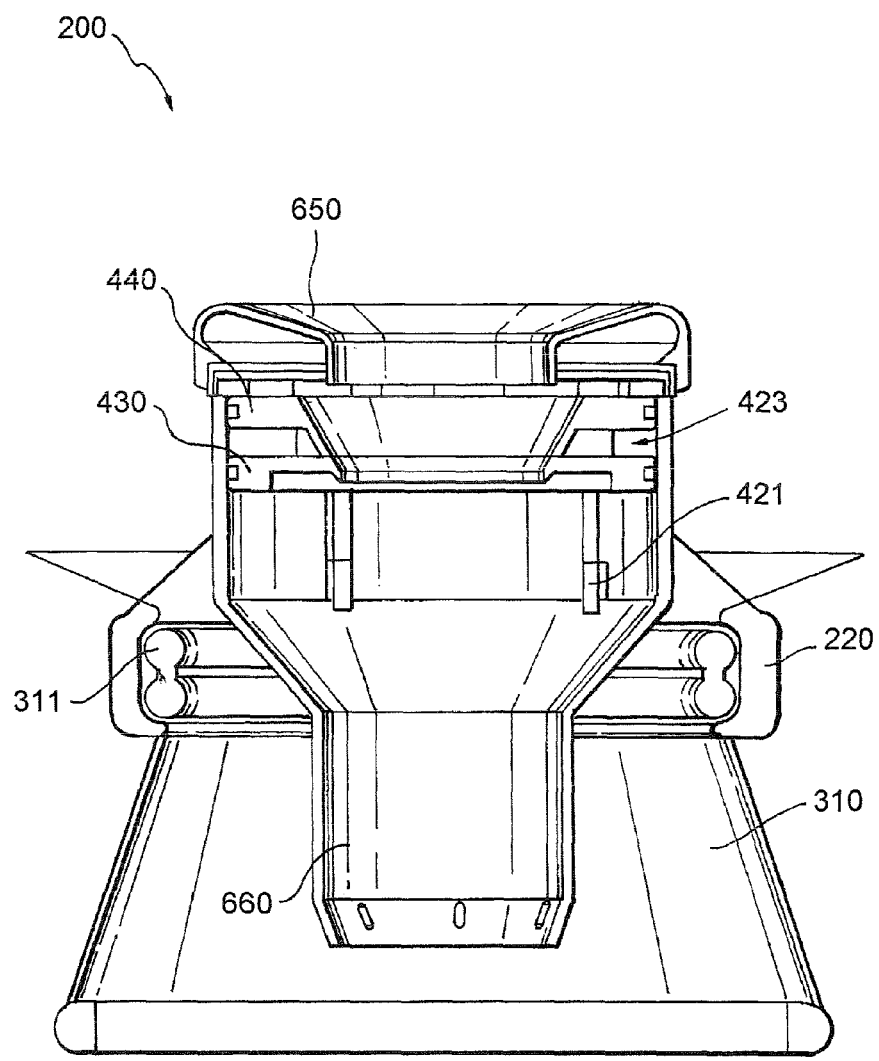
Figure 7:
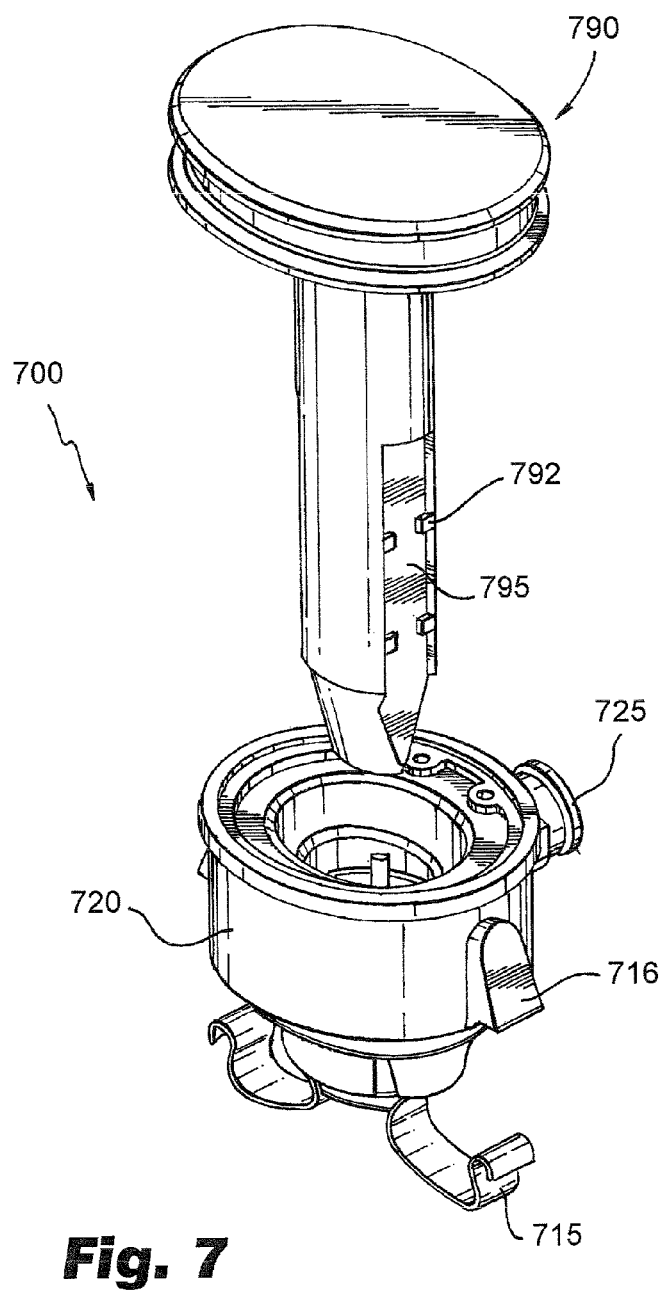
Figure 10:
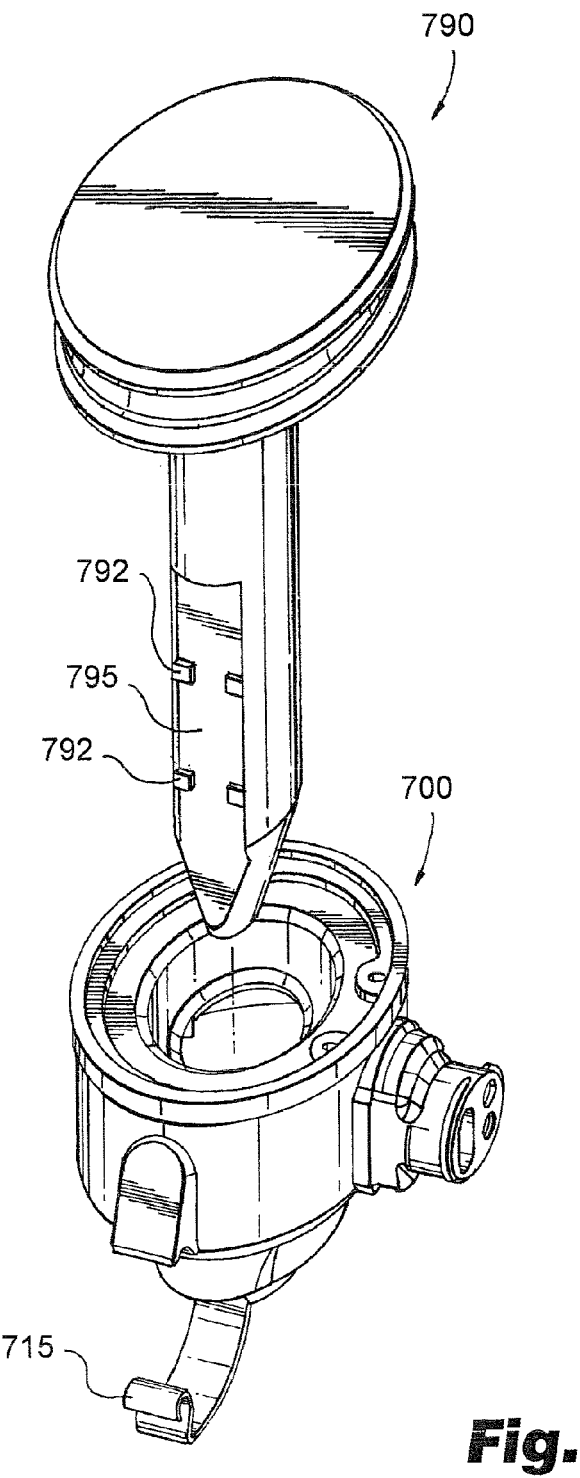
Figure 11:
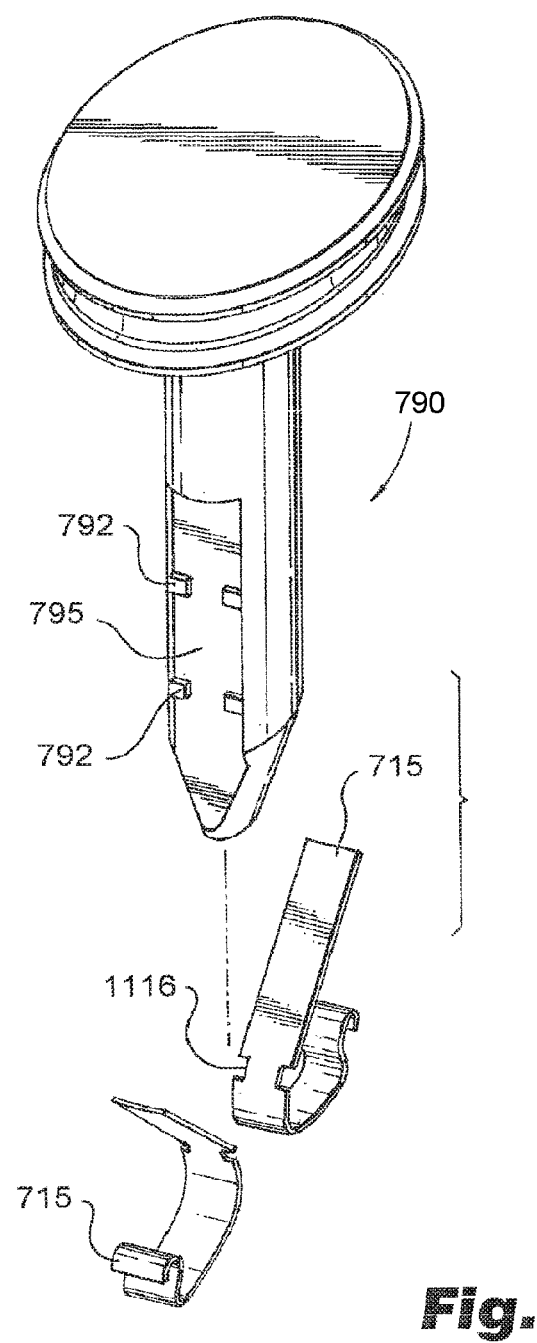

As illustrated, and as best seen in the cross-sectional views of FIGS. 4-6, a flexible wound retractor 312, which includes a sheath body 312, distal ring 313 and proximal ring 311 is seated in a distally positioned groove 429 in an expanded-diameter portion of the housing 220 of the surgical access device 200. The distal and proximal rings 311, 313 are typically made of a compliant material, such as a rubber, foam rubber or the like, and thus have an inherent shape and size. When the wound retractor 312 is inserted through an incision and secured to the patient, as by rolling or other technique, the housing 220 can be applied thereto, with the proximal ring 311 compressing initially during insertion, and then expanding to fit within the groove 429. The internal hoop stresses maintain the ring 311 and thus the retractor 312 within the groove 429, and inhibit unintentional removal therefrom.

Alternate connections between the wound retractor 310 and the housing 220 are conceived, including but not limited to use of clamp devices and the like, with the housing being seated at least partially within a lumen of the wound retractor, for example.

As with the surgical access device 100 of FIG. 1, the surgical access device 200 of FIG. 2-6 includes a housing 220, with a connector 225 extending therefrom. The internal components thereof, which will be explained in more detail below in connection with FIG. 4-6 are held within the housing by a retainer, which is embodied as a snap ring or "circlip" 260, which is used to maintain a relatively low profile, but other configurations are possible.

As best seen in the cross-sectional views of FIGS. 4-6, the surgical access device 200 is provided with a relatively low profile, allowing surgical instruments inserted therethrough to be less restricted in movement than with more conventional surgical access devices, as with the access device 100 of FIG. 1. The access device 200 includes a housing 220, adaptable with a flexible wound retractor 310 extending distally from the distal end of the housing 220.

In accordance with the invention, the access device 200 can include insufflation capability, can be adapted and configured to form a fluidic seal or barometric barrier around an instrument inserted therethrough and/or can be adapted to facilitate recirculation of insufflation gasses.

As illustrated the surgical access device 200 includes a pressurized fluid plenum 423 defined within the housing 220. In the illustrated embodiment, the plenum 423 is defined between the housing 220, a lower insert 430 and an upper insert 440. The plenum 423 is in fluid communication with at least one nozzle 428, and is configured to direct pressurized fluid in a substantially axial direction from the plenum 423 into a central lumen 418 of the wound retractor to provide a constant gaseous seal around a surgical instrument inserted therethrough, and/or across the lumen 418 when an instrument is not inserted therethrough, for example.

Similarly, as illustrated, a recirculation chamber 421 can be defined in the access device 200, between the housing 220 and the lower insert 430. One or more sealing elements, such as resilient O-rings or the like, can be provided in annular seats which are formed respectively in each of the first and second inserts 430, 440. An aperture 422 is provided in the housing 220 between the lumen 418 and the connector 225 to allow gasses to pass into a recirculation portion of a connected system.

One or more additional chambers or other fluid passageways or conduits 424 can further be provided, to facilitate fluid communication between a pressure-sensing device and/or a surgical insufflator, and the operative site. The fluid conduit can be formed within the wall of or on the inner or outer surfaces of a wound retractor connected thereto. Alternatively, a separate tube can be passed though the lumen 418 for such purpose, if so desired. In still alternate embodiments, and as illustrated in the embodiment of FIGS. 2-6 for example, a pressure sensing and/or insufflation aperture 424 can simply be in fluid communication with the upper portion of the lumen 418.

As illustrated, a connection 225 is provided on the housing 220, and has at least one channel formed therein, in fluid communication with one of the aforementioned chambers and/or conduits. It is in fluid communication with such chambers and/or conduits by passages formed therein and in the housing 220. The connection 225 facilitates connection of multiple conduits, which may be embodied in a single set, to the access device 200. The conduits, in-turn are connected to the appropriate equipment, including insufflation devices, recirculation devices and the like.

In cross-section, in a plane perpendicular to the central axis of the lumen 418, for example, the cross-section or the lumen portion of the housing 220 can be circular, oval, elliptical or otherwise oblong in shape.

As illustrated in the cross-sectional view of FIG. 6, a proximal cap 650 can be applied to the housing 220, and can incorporate sound attenuation features, such as sound absorbing materials or sound attenuation surface features to absorb, cancel or reduce sound created by fluid flowing through the lumen 418 of the access device. An internal skirt 660 is optionally provided, and is seated within the housing 220 and the lumen 418. Apertures can be formed in the housing portion of the skirt 660 to allow fluid to enter the recirculation plenum 421. Moreover, a tube or other passageway can be integrated into the skirt 660, in fluid communication with pressure sensing and/or insufflation components of attached systems, connected through the respective passageway of the connector 425.

FIGS. 7-11 illustrate a further surgical access device 700 in accordance with the invention, which includes a housing 720 with connector 725, with internal components that are substantially similar, and may include the same optional features to that of the foregoing embodiments, and which for simplicity will not be discussed in detail with respect to this embodiment. However, the surgical access device 700 includes a different anchoring mechanism than that of the foregoing embodiments. The surgical access device 700 includes spring anchors 715, which are provided in tracks formed in or alternatively on a surface of the housing 720, terminating in stops 716. The spring anchors are formed so as to secure the access device 700 to the abdominal wall of a patient, while preventing trauma thereto, and accordingly include a reverse bend at the distal end thereof. The spring anchors can be maintained within the housing 720, and not deployed, or can be deployed from a stowed position when the access device 700 is inserted. The spring anchors 715 can be formed of any suitable material including but not limited to stainless steel or shape-memory alloys.

In accordance with a preferred aspect, the access device 700 is provided with a compatible obturator 790, having opposed planar slots 795 with stubs 792 extending into the slots, offset from a bottom surface of the slots 795. As best seen in the exploded partial view of FIG. 11, notches 1116 are defines in the spring anchors 715. As the obturator 790 is advanced longitudinally, the stubs 792 pass through the notches 1116 and in combination with the slots 795 engage the spring anchors 715 and straighten them from their inherently curved configuration. The obturator 790 can be used to hold the spring anchors 715 in a straightened configuration during insertion of the access device 700, as well as during removal thereof from the patient.

Figure 12:
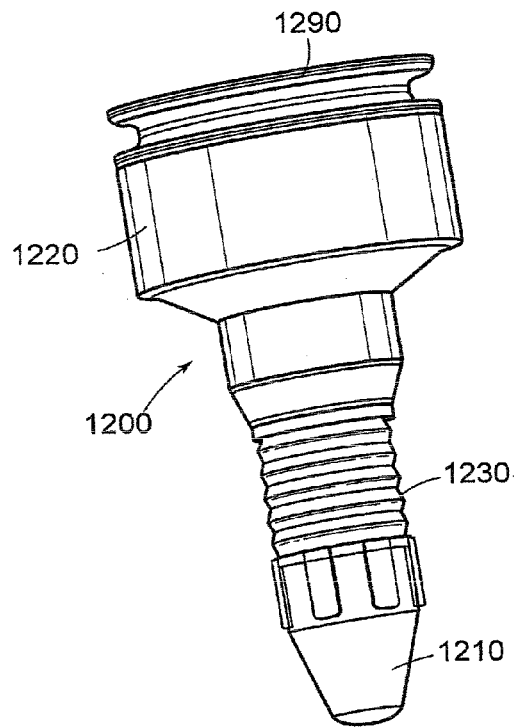
FIGS. 12 and 13 illustrate a fourth exemplary embodiment of a surgical access device in accordance with the invention, having expanding anchor elements at a distal end thereof, and a contractible body tube.
Figure 13:
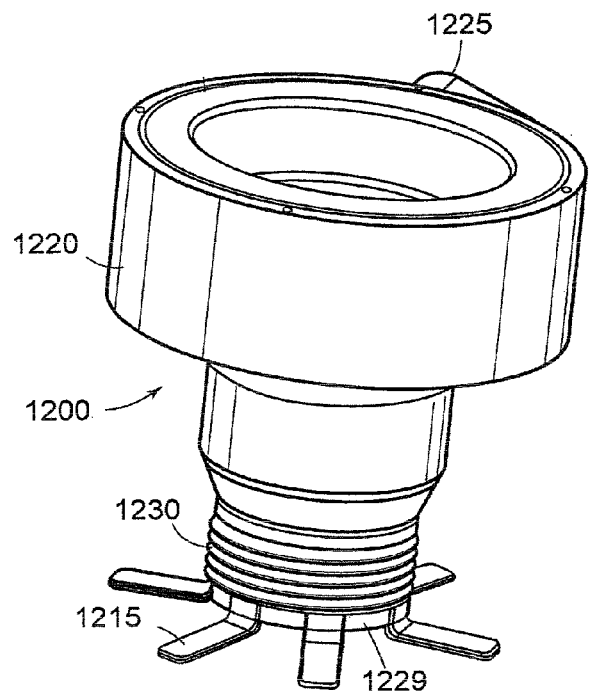
Figure 17:
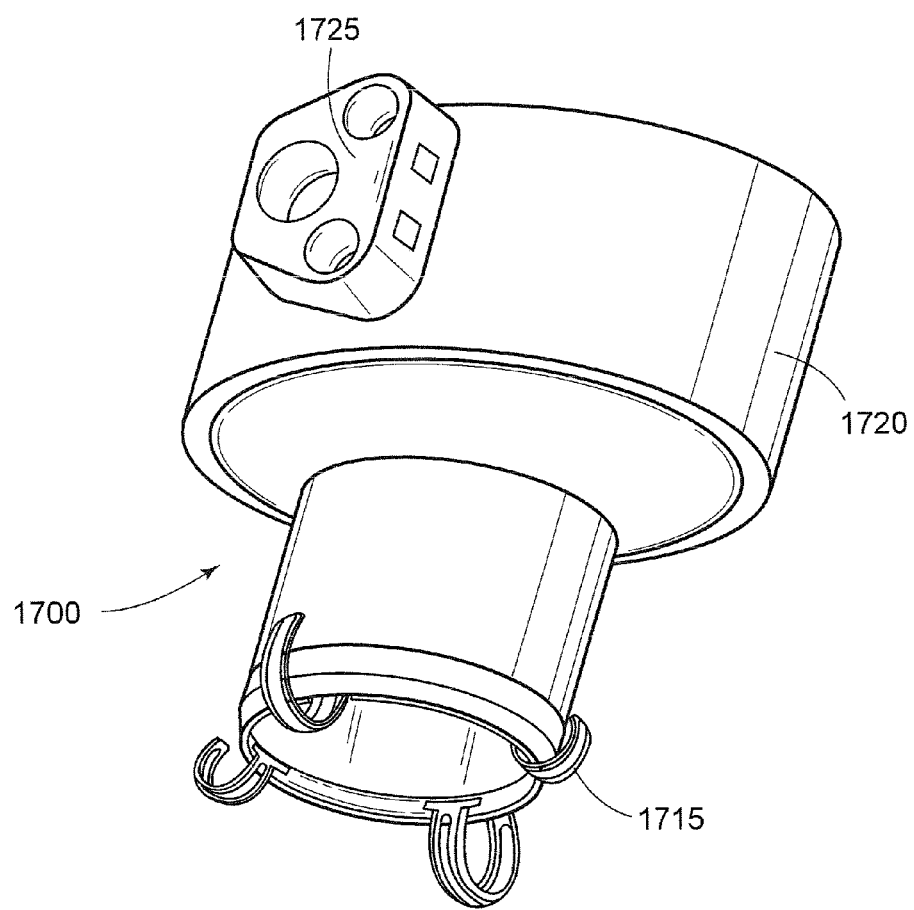

FIGS. 12-13 illustrate a further surgical access device 1200 in accordance with the invention, which includes a housing 1220 with connector 1225, with internal components that are substantially similar, and may include the same optional features to those of the foregoing embodiments, and which for simplicity will not be discussed in detail with respect to this embodiment.

The surgical access device 1200 includes still a different anchoring mechanism than that of the foregoing embodiments. The surgical access device 1200 includes spring anchors 1215, which are maintained during insertion of the access device 1200 by a distal end cap 1210, which can function as or be integrated with a surgical obturator 1290. When the access device 1200 is fully inserted into an incision formed in the abdominal wall of a patient, the cap 1210 is removed by urging the cap distally. The cap 1210 can be reapplied to the access device 1200 to allow for removal of the access device 1200.

The spring anchors 1215 can be formed of any suitable material, including shape memory alloys.

As illustrated, the body of the access device includes an adjustable bellows portion 1230 to aid in securing the access device 1200 to the abdominal wall. Following initial insertion of the access device 1200, the distal end portion 1229 of the body can be pulled proximally to effectively pinch the abdominal wall, securing the access device 1200 thereto. Such a connection can be accomplished by way of a spring-loaded component which is maintained in an extended configuration during insertion of an obturator 1290, or alternatively a cable arrangement attached to the distal end portion 1229 and pulled proximally.

FIGS. 14-16 illustrate a further surgical access device 1400 in accordance with the invention, which includes a housing 1420 with connector 1425, with internal components that are substantially similar, and may include the same optional features to those of the foregoing embodiments, and which for simplicity will not be discussed in detail with respect to this embodiment.

The surgical access device 1400 includes distal anchor elements 1415, which can be formed of any suitable material, including but not limited to stainless steel or a shape memory alloy, for example. The anchor elements 1415 are maintained in a straight orientation (FIG. 14), when engaged with a distal end portion 1410 of a surgical obturator 1490. As best seen in FIG. 15, the track 1417 is integrated with the anchor elements 1415 and is adapted to engage one or more protrusions on the obturator 1490 to maintain the anchor elements 1415 in the desired position. A frame 1416 of the anchor elements 1415 defines the overall shape, and terminates as pivots 1419. The frame 1416 can be provided with a coating 1418, which can be made of a cushioning material to minimize trauma to the patient and/or to enhance anchoring of the access device 1400. The cushioning material can be silicone rubber for example, but can be another suitable material, and can extend into a web 1481 define within the frame 1416, effectively increasing the surface area of the anchor element 1415.

FIG. 16 shows the access device 1400 with the obturator 1490 removed therefrom.

FIGS. 17-26 illustrate a further embodiment of a surgical access device 1700 in accordance with the invention, and detailed views of anchoring elements 1715 thereof. The surgical access device is similar to the embodiment of FIGS. 14-16, and includes a housing 1720 with internal components as set forth above, a connection element 1725 and anchor elements 1715.

Figure 18:
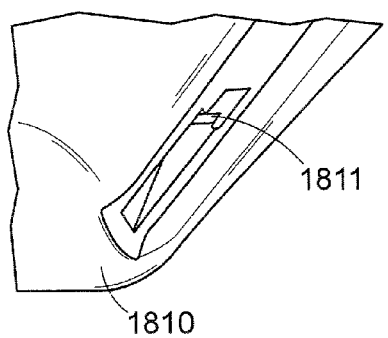
Figure 19:
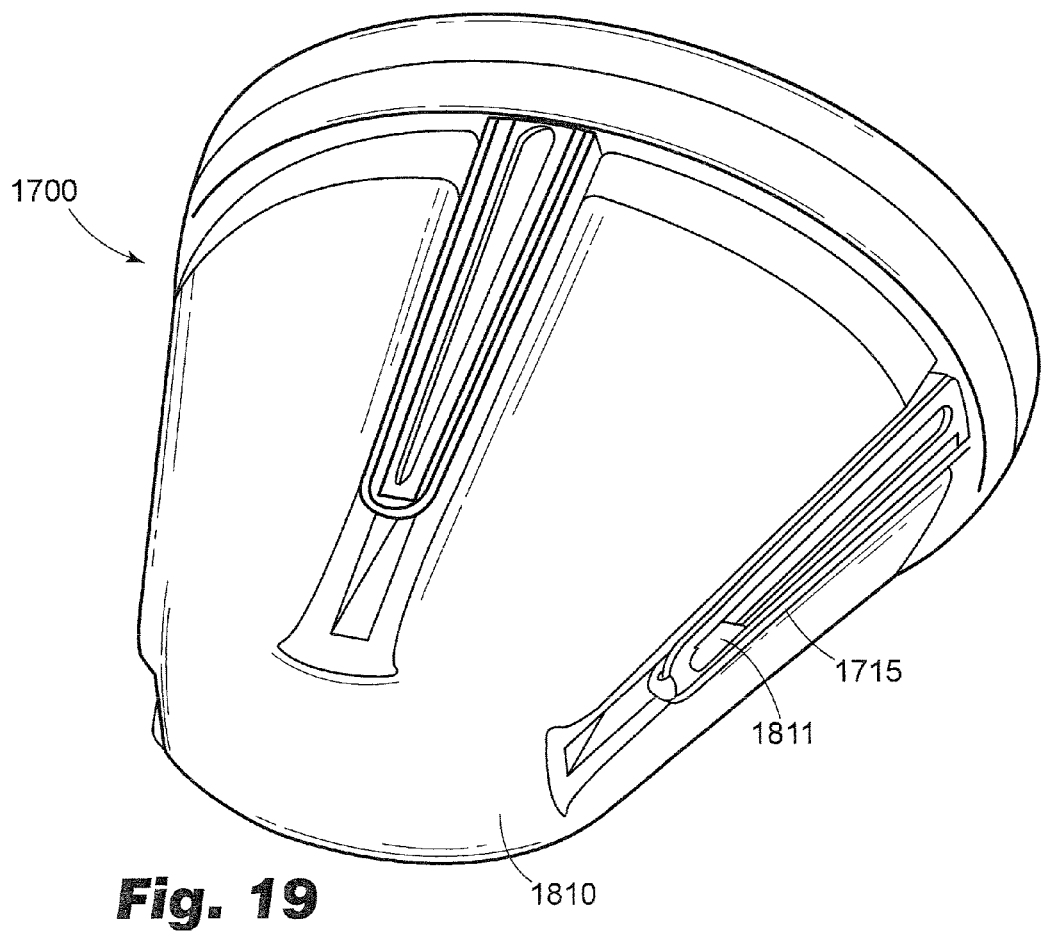
Figure 20:
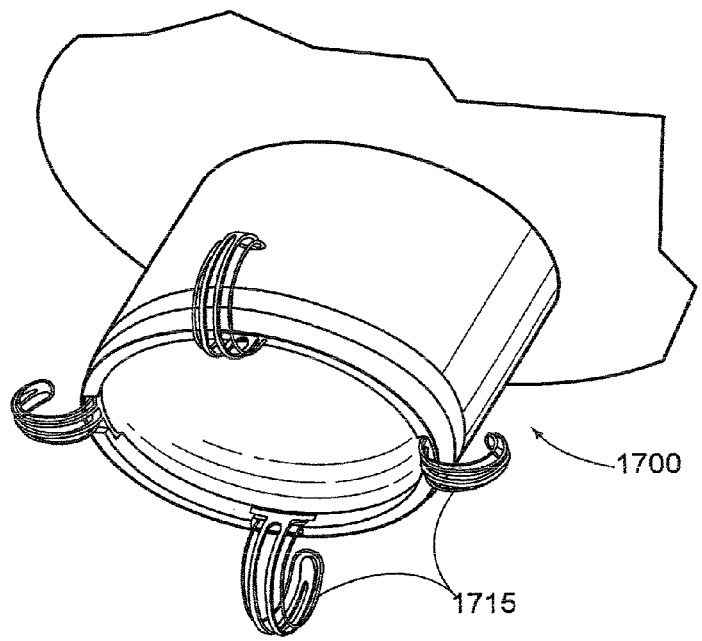

As shown in FIGS. 18 and 19, an obturator for use with the access device 1700 includes a distal end portion 1810, which engages the anchor elements 1715 by way of articulating hooks 1811. Upon insertion, the articulating hooks 1811. The anchor elements 1715 are maintained in a straight position during insertion and are released when the access device 1700 is fully inserted through the abdominal wall of the patient.

As with the access device 1400 of FIGS. 14-16, the access device 1700 includes a plurality of circumferentially arranged anchors 1715, which are formed of a material such but not limited to stainless steel or shape-memory alloys. Alternatively, with this or other embodiments described herein, resilient polymeric materials can be used. Optional features including coverings, a web element or the like can be applied to advantageous effect.

Figure 21:
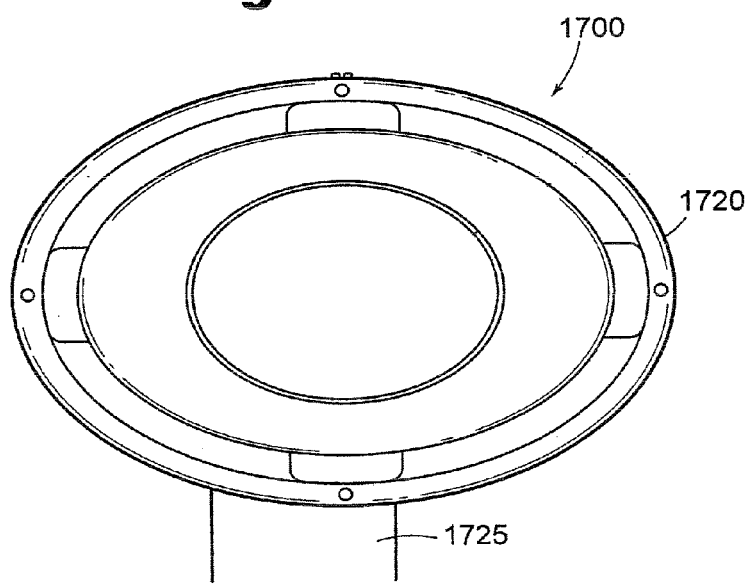
Figure 22:
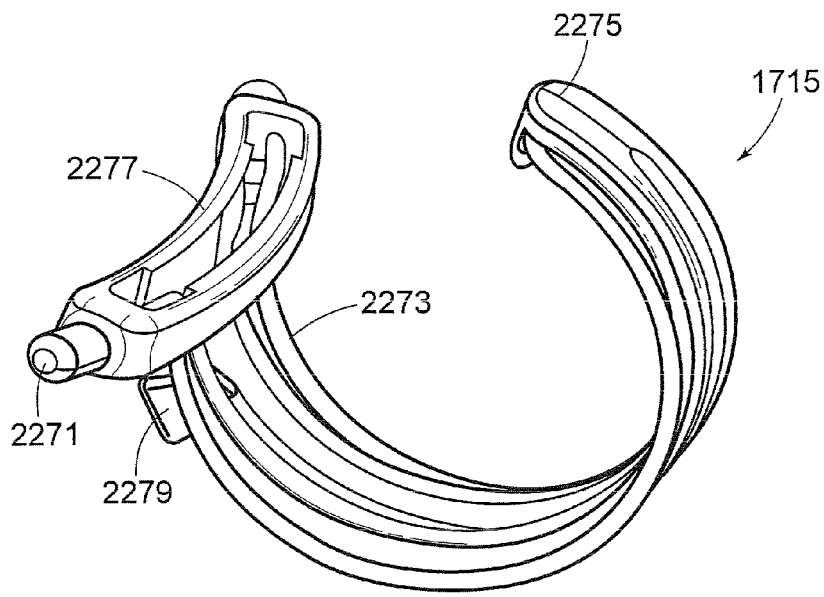
Figure 23:
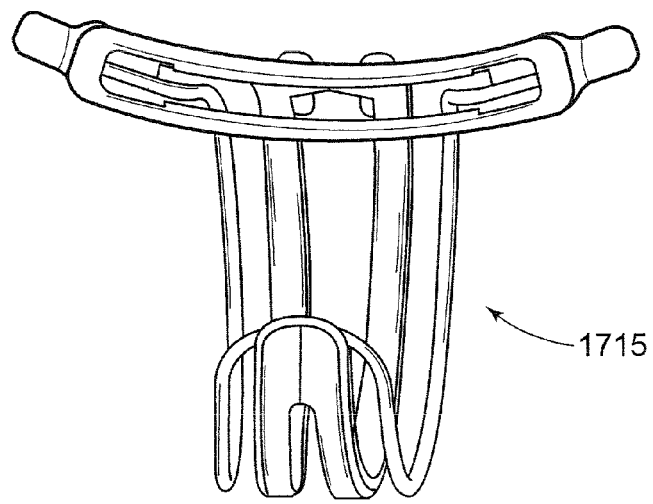

FIG. 21 is a top view of the surgical access device 1700, which illustrates an overall cross-sectional shape and lumen shaped substantially as an ellipse. As set forth above, alternate shapes are possible, including but not limited to circular, cat-eye shape or oblong of another configuration.

As best seen in FIGS. 22-26, the anchors 1715 include a main body 2275, spring elements 2273, pins 2271 extending from the body 2275, one or more struts 2277. The body 2275 can be formed of any suitable material, including but not limited to polymeric materials. The tendency of the anchors 1715 to curve is imparted in the illustrated embodiment by way of the spring elements 2273, which as with foregoing embodiments can be formed of any suitable material including but not limited to polymeric materials and metals, including shape memory alloys.

The pins 2271 are provided to secure the anchors 1715 to the body 1720 of the surgical access device 1700. Further protrusions 2279 can be provided on the anchors 1715 to additionally secure the anchors 1715 to the body 1720.

Figure 27:
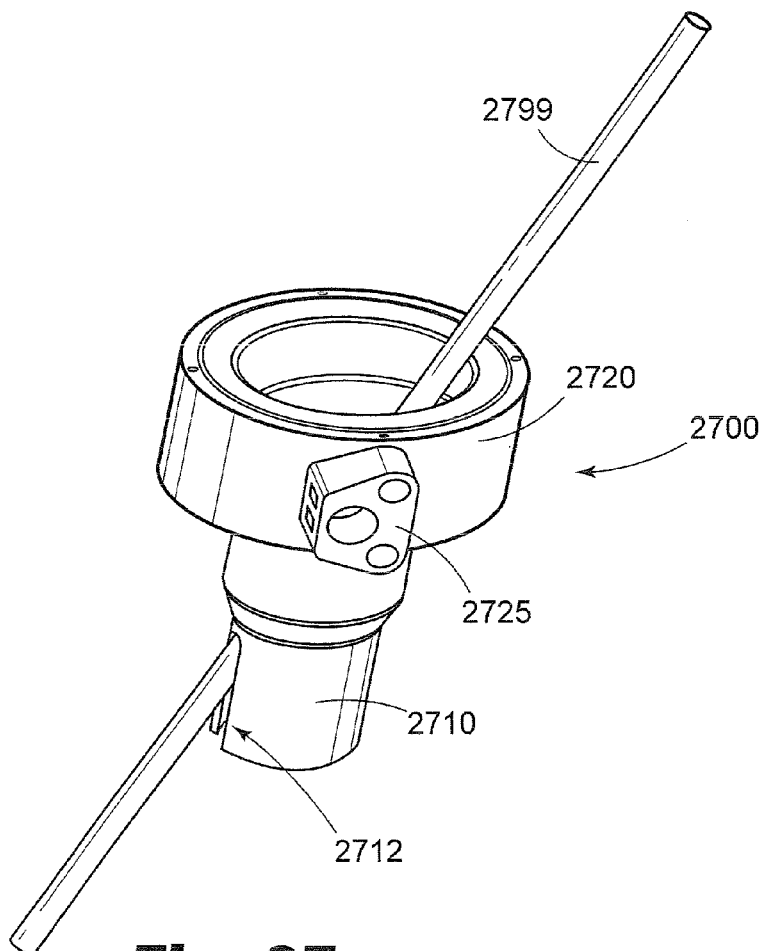
FIGS. 27-29 illustrate a seventh exemplary embodiment of a surgical access device in accordance with the invention having at least one slot formed in a distal body portion thereof to enhance a range of motion of a surgical instrument inserted therethrough.
Figure 28:
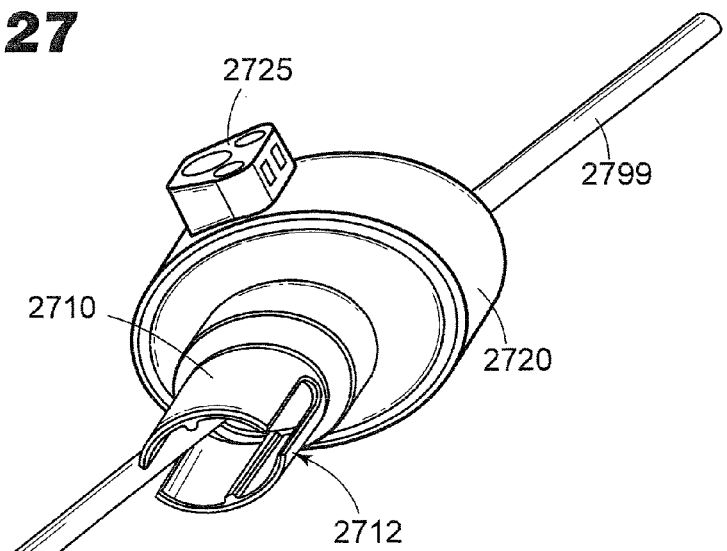
Figure 29:
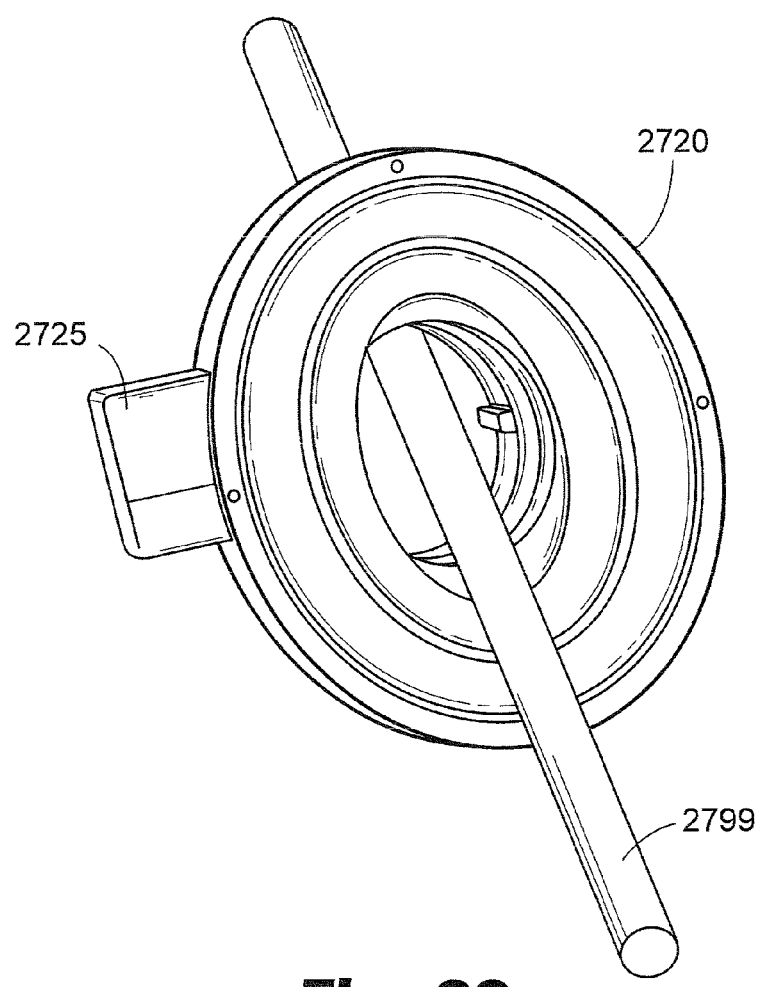
Figure 30:
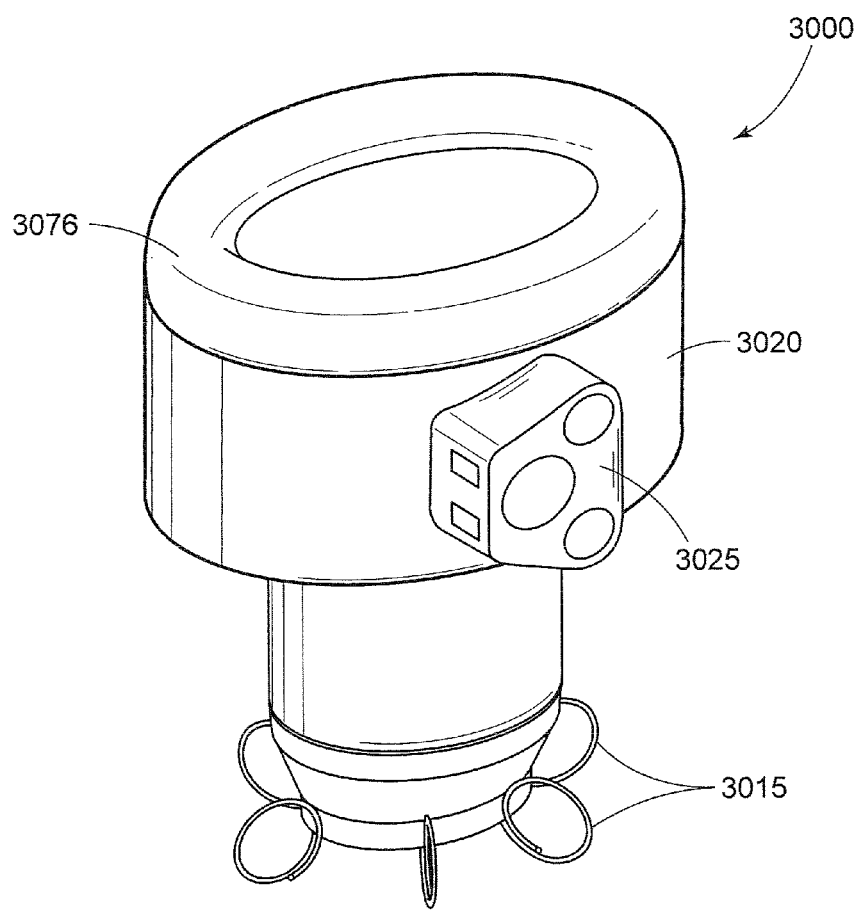
FIGS. 30-33 illustrate an eighth exemplary embodiment of a surgical access device according to the invention, having distal coiled anchor elements.
Figure 31:
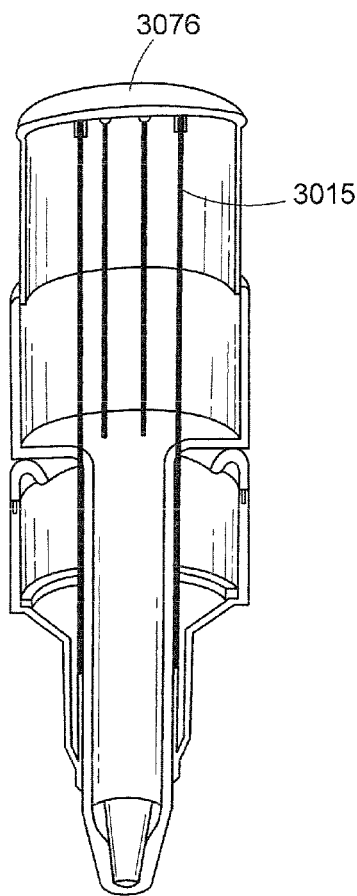
Figure 32:
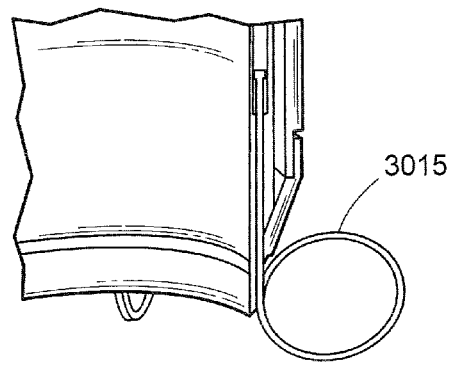
Figure 33:
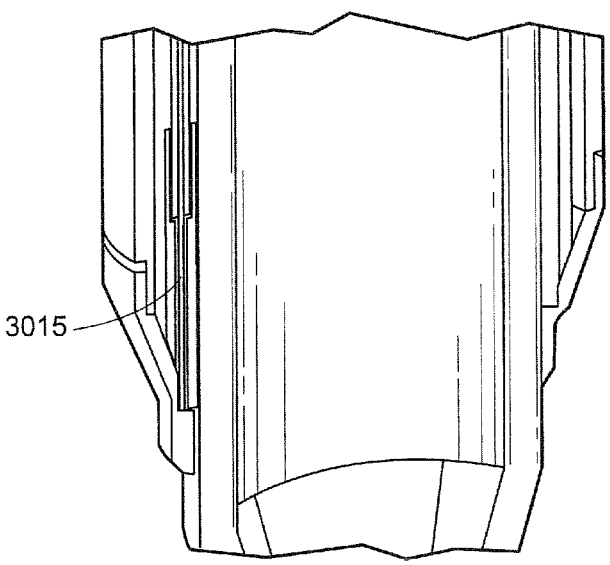

FIGS. 27-29 illustrate an access device 2700 which includes a slot 2712 formed in a distal end portion 2710 of the body 2720 thereof. This feature can be applied to any other embodiment set forth herein, which includes an elongated body. The slot allows for extended range of motion of a surgical instrument 2799 inserted through the access device 2700. As with the above-described embodiments, the housing 2720 includes a connection 2725. As best seen in FIGS. 28-29, the cross-sectional shape is substantially elliptical, but alternatively can have another shape, as mentioned above.

FIGS. 30-33 illustrate a further embodiment of a surgical access device 3000 in accordance with the invention, having a housing 3020 with connection 3025. The surgical access device 3000 includes circularly coiled anchor elements 3015 circumferentially arranged in a distal end portion thereof. An axially movable actuator 3076 is provided, in connection with the anchor elements 3015, which when contracted are housed within the body 3020 of the access device 3000. When the actuator 3076 is urged distally, the anchor elements 3015 extend from the distal end of the housing 3020, and coil in radial planes, perpendicular to a longitudinal axis of the access device 3000. When deployed, the anchor elements 3015 abut the abdominal wall, thereby helping anchor the access device 3000. As with foregoing embodiments, the anchor elements 3015 can be formed of a spring material, which can be, for example, a resilient polymeric material, or a metal such as stainless steel or a shape memory alloy.

Figure 34:
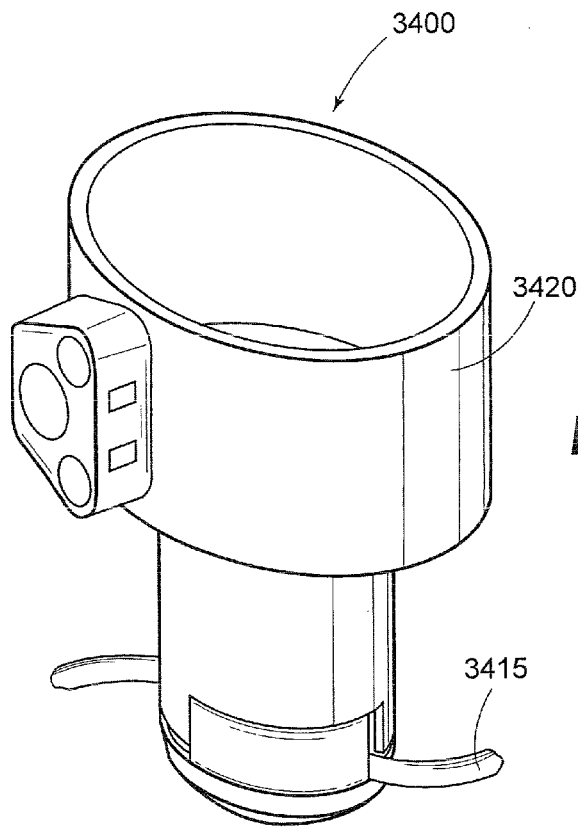
FIGS. 34 and 35 illustrate a surgical access device with radially deployable anchor elements actuated by one or more shafts.
Figure 35:
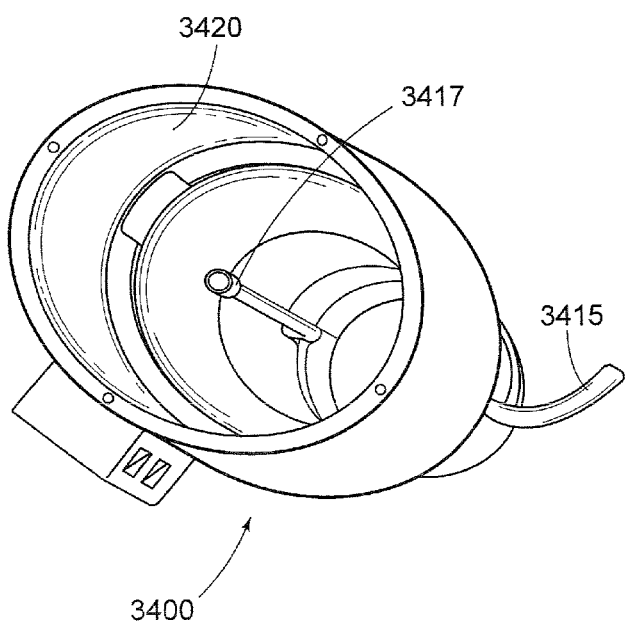

FIGS. 34 and 35 illustrate a surgical access device 3400 having yet a further alternative anchoring mechanism, with radially deployable anchor elements 3415, actuated by one or more shafts 3417 provided in a housing 3420 thereof. When the access device is inserted through an incision, the anchor elements 3415 are deployed to anchor the access device 3400 to the abdominal wall of the patient.

As mentioned above, compatible features described in connection with one embodiment of the invention can advantageously be incorporated with other embodiments of the invention. The devices and related methods of the present invention, as described above and shown in the drawings, provide surgical access devices with advantageous properties including anchoring capabilities without causing excessive trauma to the patient. It will be apparent to those skilled in the art that various modifications and variations can be made in the devices, systems and related methods of the present invention without departing from the spirit or scope of the invention.

What is claimed is:

1. A surgical access device comprising a proximal housing having proximal and distal end portions, the distal end portion of the housing being configured and adapted to engage a proximal portion of a flexible wound retractor, the proximal housing having a plenum chamber being defined in the proximal housing, the plenum chamber being in fluid communication with at least one nozzle, configured to direct pressurized fluid in an axial direction from the plenum chamber into a central bore of the surgical access device to provide a constant gaseous seal around a surgical instrument inserted therethrough, while inhibiting a loss of pressurized fluid from the body cavity therethrough, and wherein the plenum chamber is adapted and configured to receive pressurized fluid and conduct the pressurized fluid to the at least one nozzle and wherein the distal end portion of the housing and proximal portion of the flexible wound retractor are adapted and configured to detachably engage with one another.

* * * * *